(12) United States Patent
Chateau et al.

(10) Patent No.: US 6,379,008 B1
(45) Date of Patent: Apr. 30, 2002

(54) METHOD OF DETERMINING THE SHAPE OF AN OPTHALMIC CONTACT LENS FOR CORRECTING OPTICAL ABERRATIONS OF THE EYE BEYOND DEFOCUSING OR ASTIGMATISM AND SYSTEM FOR IMPLEMENTING THE METHOD

(75) Inventors: Nicolas Chateau, Paris; Gildas Marin, Antony; Bruno Fermigier, Paris, all of (FR)

(73) Assignee: Essilor International (Compagnie Generale d'Optique), Paris (FR)

( * ) Notice: Subject to any disclaimer, the term of this patent is extended or adjusted under 35 U.S.C. 154(b) by 0 days.

(21) Appl. No.: 09/663,695

(22) Filed: Sep. 22, 2000

(30) Foreign Application Priority Data

Sep. 22, 1999 (FR) ............................................. 99 11843

(51) Int. Cl.[7] .................................................. A61B 3/00
(52) U.S. Cl. ....................................................... 351/247
(58) Field of Search .................................. 351/212, 219, 351/246, 247, 160 R, 161, 177; 128/898

(56) References Cited

U.S. PATENT DOCUMENTS

| 5,114,628 | A | | 5/1962 | Höfer et al. |
| 4,863,260 | A | | 9/1989 | Gersten et al. |
| 4,878,750 | A | | 11/1989 | Sekiguichi |
| 5,570,142 | A | * | 10/1996 | Lieberman ............... 351/160 R |
| 6,095,651 | A | * | 8/2000 | Williams et al. ............. 351/246 |

FOREIGN PATENT DOCUMENTS

EP 0 374 306 6/1990

* cited by examiner

Primary Examiner—George Manuel

(57) ABSTRACT

A method of determining the shape of an ophthalmic contact lens for correcting optical aberrations of the eye beyond defocusing or astigmatism includes the steps of measuring the optical aberrations of the eye to be corrected, determining the shape of the rear face of the lens from the measured topography of the cornea in order to obtain a predetermined mechanical behavior of the lens when it is placed on the eye, measuring the optical aberrations of the eye to be corrected, and determining the shape of the front face of the lens from the measured optical aberrations of the eye to be corrected combined with data relating to the shape determined for the rear face of the lens in order to correct the aberrations. The system includes measurement units for measuring the topography and the aberrations of the eye and an electronic calculator unit.

20 Claims, 1 Drawing Sheet

METHOD OF DETERMINING THE SHAPE OF AN OPTHALMIC CONTACT LENS FOR CORRECTING OPTICAL ABERRATIONS OF THE EYE BEYOND DEFOCUSING OR ASTIGMATISM AND SYSTEM FOR IMPLEMENTING THE METHOD

BACKGROUND OF THE INVENTION

1. Field of the Invention

The invention relates generally to the design of ophthalmic contact lenses and more precisely to a method of determining the shape of an ophthalmic contact lens capable of correcting optical aberrations of the eye beyond defocusing or astigmatism. It also relates to a system for implementing the method.

2. Description of the Prior Art

Existing ophthalmic contact lenses, despite all the advances in their design, merely correct the coarsest optical defects of the eye, namely defocusing and astigmatism. It has long been known in the art that the eye can suffer from additional defects resulting from higher order optical aberrations, of a more refined nature, affecting the various components of the eye: cornea, lens or intraocular media. These higher order optical aberrations of the eye disrupt the image formed on the retina, which interfere with vision even after any defocusing or astigmatism defects have been corrected. In some pathological cases of irregular corneas, for example keratoconus, these aberrations make it practically impossible to see shapes.

Ophthalmic measuring techniques have recently been developed for accurately measuring higher order optical aberrations of the eye, in addition to the standard defects of defocusing and astigmatism. For example, U.S. Pat. No. 5,777,719 proposes a method and system for accurately measuring optical aberrations of the eye by analyzing a laser wavefront reflected by the retina of the eye using the Hartmann-Shack method. It is theoretically possible to determine from this measurement the shape of an ophthalmic contact lens for compensating the measured aberrations. This technique personalizes the lens to the particular optical aberrations of the eye of the patient.

Thought has therefore been given to a method of determining the shape of an ophthalmic contact lens for correcting optical aberrations of the eye including a step of measuring the optical aberrations of the eye to be corrected and a step of determining the shape of said lens to correct those aberrations from the measured optical aberrations of the eye to be corrected.

The front face of a contact lens is the convex face of the lens, which is on the opposite side of the lens to the eye, and the rear face of a lens is the concave face of the lens, which is in contact with the eye.

However, at this stage it was realized that a lens designed on the basis of the above data alone does not provide the hoped-for compensation when it is installed on the eye of the patient.

The lenses generally have a rear face of simple shape in which only the central radius of curvature is matched to the surface of the cornea. The cornea usually has a complex shape that varies from one person to another. The difference in shape between the cornea and the rear face of the lens produces several effects. It causes deformation of the lens and creates an irregular thickness film of tears between the lens and the cornea. These two effects induce additional unwanted aberrations that degrade visual performance.

Another form of personalization of ophthalmic contact lenses is known in the art. It is known in the art that the surface of the cornea is not perfectly regular but, to the contrary, is generally asymmetrical and aspherical. Depending on its degree and its nature, this surface irregularity of the cornea can be a source of conflict between the surface and the rear surface of the contact lens, which is generally perfectly regular, spherical, circular aspherical or toroidal. This is uncomfortable for the wearer, sometimes leading to irritation of the cornea and rejection of the lens, forcing the patient to use eyeglasses in preference to contact lenses. Making contact lenses whose rear face is "adapted" to the irregular surface of the cornea is one proposal for solving this problem, for example in U.S. Pat. No. 5,570,142. The "adaptation" consists of a corresponding relationship of shape between the posterior surface of the lens and the surface of the cornea, which can be complete, over all of the posterior surface of the lens, or partial, localized at the periphery of the lens, to provide a stable and regular seating for the lens on the cornea.

However, regardless of the manner in which the posterior surface of the lens is adapted to the surface of the cornea, personalized adaptation merely improves the comfort of the wearer or prevents rotation of the lens on the eye, and does not take any account of ocular aberrations.

In the light of the above information, the object of the invention is to conceive a method of determining the shape of a personalized ophthalmic contact lens which is capable, when installed on the eye of the patient, of correcting the higher order aberrations measured on the eye concerned by limiting the generation of unwanted aberrations.

SUMMARY OF THE INVENTION

The invention proposes a method of determining the shape of an ophthalmic contact lens for correcting optical aberrations of an eye, which method includes the steps of:

measuring the optical aberrations of the eye to be corrected, determining the shape of the front face of said lens from the measured optical aberrations of the eye to be corrected in order to correct said aberrations, measuring the topography of the cornea of the eye to be corrected, and determining the shape of the rear face of the lens from the measured topography of the cornea in order to limit the generation of unwanted aberrations when the lens is placed on the eye, and in which method, to determine the shape of the front face of the lens, data relating to the shape determined for the rear face of the lens is combined with the measured optical aberrations of the eye.

Knowing the wavefront to be corrected, the shape of the rear face, the wavelength, the index of the material and the thickness at the center, the required shape of the front face can be calculated by solving the converse problem of three-dimensional ray tracing.

The above method takes into account a constraint of fundamental practical importance previously unidentified in the context of correcting higher order optical aberrations of the eye. To correct higher order aberrations of the eye by means of a contact lens it is not sufficient to measure the aberrations and to design the shape of the front face of the lens so that it corrects those aberrations. It is also necessary to avoid, or at least to control, in order to take them into account, the deformations of the lens on the eye and the irregular thickness of the film of tears between the cornea and the lens. The fact that the rear face of the lens designed by the method of the invention is personalized provides total control over these two essential parameters, namely the deformation of the lens and the thickness of the layer of tears, on the basis of the measured topography of the cornea. Clearly these two parameters condition the effective optical correction achieved by the lens. Controlling them is therefore essential in the context of correcting higher order aberrations of the eye in that such correction is by its very nature much more refined than merely correcting defocusing or astigmatism, and consequently requires high precision in the shape of the lens, not only in vitro, that is to say during manufacture, but also in vivo, that is to say when it is in place on the eye of the patient.

The mechanical behavior of lens in vivo is therefore controlled by a particular design of the rear face of the lens. The particular shape of that face must be taken into account in designing the front face of the lens, which in the final analysis determines the global optical correction applied by the lens. The shape of the rear face of the lens conditions the optical characteristics of the lens itself and also the thickness of the film of tears, which may be irregular (but controlled), and which has a decisive effect on the global optical correction obtained.

The shape of the rear face of the lens can be designed so that there is a film of tears of constant thickness between the lens and the cornea. In another embodiment, this face is designed so that the thickness of the film of tears increases with the distance away from the center of the lens.

The topography of the cornea of the eye to be corrected and the aberrations of said eye to be corrected are preferably measured in a common spatial frame of reference. To be more precise, the common spatial frame of reference comprises a first axis coincident with the main line of vision of the eye to be corrected, a horizontal second axis orthogonal to the first axis and a third axis orthogonal to the first and second axes. The main line of vision corresponds to the line passing through the fixing point in the instrument and the center of the pupil of the eye.

In accordance with another advantageous aspect of the invention, to improve the optical correction further, in particular for certain patients requiring increased precision, the method can further include the steps of:

fabricating a test lens having front and rear faces conforming to those determined by the aforementioned steps, measuring in vivo the optical aberrations of the optical system comprising the eye to be corrected fitted with the fabricated test lens, and correcting the shape of the front face of the lens on the basis of data relating to the initially determined shape of the test lens and the new measured optical aberrations of the eye fitted with the test lens.

The invention also provides a system for implementing the above method, the system including:

a measuring unit for measuring the topography of the cornea of the eye to be corrected and delivering digital data representative of that topography, a measuring unit for measuring the aberrations of the eye to be corrected and delivering digital data representative of those aberrations, and an electronic calculator unit adapted to determine the shapes of the front and rear faces of the lens from data supplied to it by the measurement unit for measuring the topography of the cornea of the eye to be corrected and the measurement unit for measuring the aberrations of said eye to be corrected and to deliver digital data representative of those shapes.

According to another advantageous aspect of the invention, the method can be simplified in certain specific pathological cases by having the step of measuring the aberrations of the eye to be corrected coincide with the step of measuring the topography of the cornea of said eye to be corrected, the aberrations being deduced by calculating the measured topography of said cornea.

The above type of method can be advantageous if the aberrations of the cornea are dominant, which has already been observed.

In this case, the system for implementing the above method includes:

a measuring unit for measuring the topography of the cornea of the eye to be corrected and delivering digital data representative of that topography, and an electronic calculator unit adapted to estimate the aberrations produced by the cornea from the data supplied by the measurement unit for measuring the topography of the cornea and to determine the shapes of the front and rear faces of the lens from data supplied to it by the measurement unit for measuring the topography of the cornea and the estimated aberrations and to deliver digital data representative of those shapes.

One or other of the above systems can advantageously further include a unit for fabricating a lens from digital data supplied to it by the calculator unit. This provides a complete system for fabricating a personalized contact lens, which system can be fully automated.

Other features and advantages of the invention will become apparent on reading the following description of particular embodiments of the invention, provided by way of non-limiting example.

The description refers to the accompanying drawings.

DETAILED DESCRIPTION OF THE PREFERRED EMBODIMENTS

Figure 1:
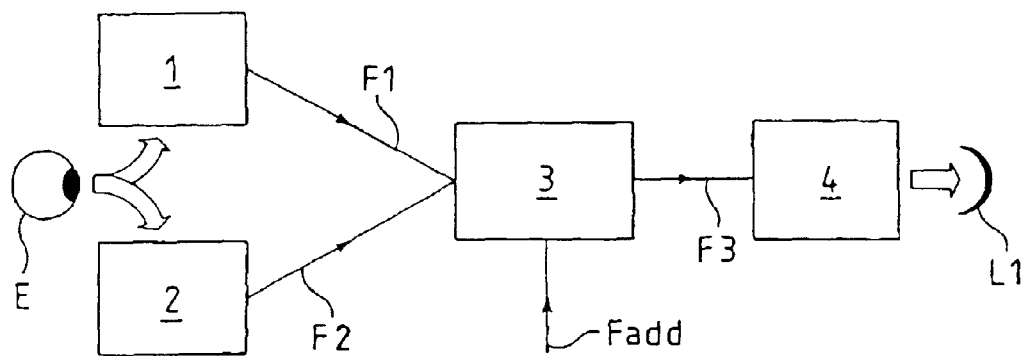
FIG. 1 is a diagram showing a system for fabricating a contact lens from measurements of the topography of the cornea and of optical aberrations of the eye to be corrected, using a first embodiment of the method and the system in accordance with the invention for determining the shape of a lens.

Referring to FIG. 1, a system for determining the shape of an ophthalmic contact lens for correcting high order aberrations of the eye includes:

a unit 1 for measuring the topography of the cornea of the eye E to be corrected, delivering digital data representative of that topography, a unit 2 for measuring the aberrations of the eye E to be corrected, delivering digital data representative of those aberrations, and an electronic calculator unit 3 adapted to determine, from data supplied to it by the unit 1 for measuring the topography of the cornea of the eye to be corrected and the unit 2 for measuring the aberrations of said eye to be corrected, the shapes of the front and rear faces of the lens, delivering digital data representative of those shapes.

The system is complemented by a unit 4 for fabricating a contact lens L1 based on data supplied by the calculator unit 3. This provides a complete system for fabricating personalized contact lenses, which system is entirely automated.

The unit 1 for measuring the topography of the cornea can take various forms known in the art and available off the shelf. The following systems could be used, for example:

Placido disk topographers: Tomey TMS-1 (Computed Anatomy), EyeSys Corneal Analysis System (EyeSys Laboratories), triangulation topographers (rasterstereography): PAR Technology Corneal Topography System (PAR Technology), Orbscan (Orbtek).

The various existing systems for measuring the corneal topography are described in the following article: T. Dave, "Current developments in measurement of corneal topography", Contact Lens and Anterior Eye 21, pp. S13–S30 (1998 ).

Whatever system it uses, the unit 1 for measuring the topography of the cornea must supply data for the greatest possible portion of the surface of the eye that will be covered by the lens. It is desirable to obtain the elevation distribution of the cornea and part of the sclera. This is possible with the Maastricht Shape topographer in particular, which is a system using projection of Moiré fringes sold in the USA and described in the following documents:

Jongsma F. H. M., Laan F. C., Stultiens B. A. T., "A Moiré based corneal topographer suitable for discrete Fourier analysis", SPIE Vol. 2126, Ophthalmic Technology 4, 1994 : 185–92. M.C;

Corbett, D. P. O'Brart, B. A. Stultiens, F. H. Jongsma, J. Marshall, "Corneal topography using a new Moiré image-based system", Eur. J. Implant Ref. Surg. 7, 353–70 (1995).

All the above topographers are able to supply an electronic file containing the coordinates of points on the cornea in digital form.

The unit 2 for measuring the optical aberrations of the eye E can also take various forms. The following systems in particular can be used:

a subjective method device of the type described in the following documents:
M. S. Smirnov, "Measurement of the wave aberration of the human eye". Biophysics 6, 776–794 (1961);
He J C, Marcos S, Webb R H, Burns S A. "Measurement of the wave-front aberration of the eye by a fast psychophysical procedure", J. Opt. Soc. Am. A 15 (9)2449–2456 (1998 );

a system using the Foucault test method, of the type described in the following document: F. Berny and S. Slansky, "Wavefront determination resulting from Foucault test as applied to the human eye and visual instruments", in Optical Instruments and Techniques, J. H. Dickenson, ed. (Oriel, Newcastle, UK, 1969), pp. 375–386;

an aberroscope, as described in the following document: H. C. Howland and B. Howland, "A subjective method for the measurement of monochromatic aberrations of the eye", J. Opt.Soc.Am. 67, 1508–1518, (1977);

a Hartmann-Shack wavefront sensor device of the type described in the following documents:
"A new method to precisely measure the wave aberrations of the human eye with a Hartmann-Shack wavefront sensor", Phd. Dissertation, J. Liang, University of Heidelberg (1991);
J. Liang, B. Grimm, S. Goelz, & J. F. Bille, "Objective measurement of Was of the human eye with the use of a Hartmann-Shack wave-front sensor", J. Opt. Soc. Am. A. 11, 1949–1957 (1994);
J. Liang, and D. R. Williams, "Aberrations and retinal image quality of the normal human eye", J. Opt. Soc. Am. A 14, 2873–2883 (1997).

It can be particularly advantageous to use for the unit 2 for measuring the optical aberrations of the eye a Hartmann-Shack wavefront sensor system, as mentioned above, in that the method used in that system is totally objective and relatively simple and quick to use.

All the above systems are naturally able to supply a file containing digital data representative of the measured ocular aberrations of the eye.

The electronic calculator unit 3 can take the form of a microcomputer running software whose functions are described below, for example.

The fabrication unit 4 can be a direct asymmetrical numerically controlled machine tool of sub-micron precision, as used at present to fabricate contact lenses. Other processes can be used, for example index gradient creation.

Whatever fabrication process and machine are used, the fabrication unit 4 is in any event of the digital type, i.e. it is capable of automatically fabricating a lens from digital data representative of the shape of the lens to be fabricated received as input data.

Note that a machine tool has the following limitations. First of all, the tool radius used imposes a limit on the curvature of the surfaces on the lens in the radial direction. Also, the maximum acceleration and amplitude of asymmetrical vibrations of the lens respectively limit the offset relative to rotational symmetry and the curvature of the surfaces in the tangential direction. Finally, linearity errors arise between the input data supplied to the machine by the calculator unit 3 (representative of the calculated and required shape of the lens) and the lens shape actually produced by the machining operation.

It is preferable to take these various limitations into account in calculating the front and rear faces of the lens, i.e. in practice in the operating software of the calculator unit 3, in order to avoid commanding the fabrication unit 4 to fabricate a lens with face geometries that could not be achieved and to compensate systematically errors generated by the machine tool.

The various elements of the system can be at different locations and connected by a network.

The system that has just been described operates in accordance with the method according to the invention in the following manner.

The unit 1 for measuring the topography of the cornea and the unit 2 for measuring the aberrations of the eye are placed in succession in front of the eye E to be corrected to perform their respective measurements. The two units 1 and 2 use a common spatial frame of reference (not shown in the figures) for those measurements, including the following three axes: a first axis coincident with the main line of vision of the eye (straight line passing through the center of the pupil and through the fixing point of the instrument), a horizontal second axis orthogonal to the first axis, and a third axis orthogonal to the first and second axes. Of course, using this common spatial frame of reference presupposes that each of the two measuring units 1 and 2 has a fixing point and that it is possible to determine the position of the center of the pupil and of the fixing point relative to the other data measured.

When they have performed their measurements, the measurement units 1 and 2 each deliver digital data representative of the result of the measurements. Thus the measurement unit 1 delivers digital data representative of the topography of the cornea of the eye E and the measurement unit 2 delivers digital data representative of the optical aberrations of the eye E. That data is transmitted to the electronic calculator unit 3, as shown by the arrows F1 and F2 in FIG. 1.

From that data the electronic calculator unit 3 calculates the shape of the front and rear faces of the lens.

To be more precise, the electronic calculator unit 3 determines the shape of the lens in the following manner. From the data relating to the topography of the cornea of the eye E1 supplied to it by the measurement unit 1, the electronic calculator unit 3 calculates the shape of the rear face of the lens to obtain a predetermined mechanical behavior of the lens when it is installed on the eye. To this end, the calculator configuration of the rear face of the lens can correspond either exactly to that of the surface of the cornea or to a mathematical transformation of that surface. The procedure explained in U.S. Pat. No. 5,570,142 can be used, for example.

The shape of the rear face of the lens could be designed so that there is a constant thickness film of tears between the lens and the cornea. In another embodiment, that face is designed so that the thickness of the film of tears increases with the distance from the center of the lens.

At this stage the clinician can be given the opportunity to choose the mathematical transformation used to deduce the shape of the rear face from the topography of the cornea.

Whatever calculation mode is adopted, the shape of the rear face of the lens is intended to avoid deformation of the lens on the eye and irregularities in the thickness of the film of tears between the cornea and the lens, or at least to control them, i.e. to identify them and quantify them so that they can be allowed for. Thus the final shape of the rear face of the lens installed on the eye and the thickness of the film of tears are predetermined and stored in memory by the electronic calculator unit 3.

The electronic calculator unit 3 then calculates the shape of the front face of the lens in order to confer on the lens the required optical correction characteristics. The shape of the front face of the lens is calculated from data relating to the optical aberrations of the eye E supplied by the measurement unit 2 and data relating to the previously calculated shape of the rear face of the lens. It is essential to combine the data relating to the shape imparted to the rear face of the lens to the data relating to the measured aberrations of the eye in order to calculate the shape of the front face of the lens, because the optical correction provided by the lens depends on the shape of the front and rear surfaces of the lens and on the thickness (possibly the irregular thickness) of the film of tears between the lens and the cornea. If necessary, the electronic calculator unit 3 processes the data that it has previously stored on the shape in vivo, after possible deformation of the lens, of the rear face of the lens and the resulting thickness of the film of tears.

Also, in calculating the shapes of the front and rear faces of the lens, the electronic calculator unit 3 can take account of additional data entered manually by an operator or input in the form of a digital data file, as symbolized by the arrow Fadd.

Accordingly, to determine the shape of the front face of the lens, allowance is made for the subjective refraction of the patient whose eye is to be corrected. To be more precise, the subjective refraction power is substituted by calculation for the objective refraction power contained in the data resulting from measuring the ocular aberrations of the eye.

Similarly, the refractive index of the material of the lens is taken into account in determining the shape of the front face of the lens.

Equally, additional specific correction data that is combined with the measured optical aberrations are taken into account in determining the shape of the anterior face of the lens. In particular, if the eye to be corrected suffers from presbyopia, the additional data introduces a complex multifocal correction.

Also, the mechanical characteristics of the material of the lens, and in particular its constants of elasticity and viscosity, are taken into account in determining the shape of the rear face of the lens.

Finally, as previously mentioned, the means provided for fabricating the lens and the limitations imposed by those means on the possible shape of the front and rear faces of the lens are taken into account in determining the configurations of the front and rear lens.

After the above calculations, the electronic calculator unit 3 supplies a digital data file representative of the configurations of the front and rear faces of the lens. As shown by the arrow F3 in FIG. 1, that file is transmitted to the fabrication unit 4 which automatically fabricates a contact lens L1 whose front and rear faces conform to the data contained in the file transmitted.

Figure 2:
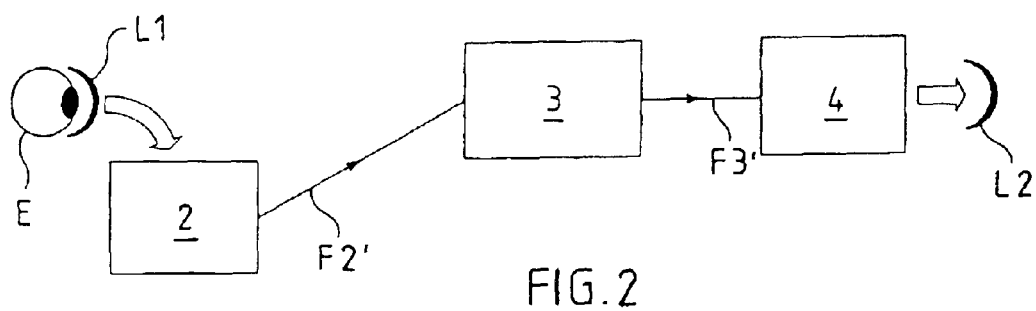
FIG. 2 is a diagram showing the use of the system shown in FIG. 1 to refine the shape of the lens on the basis of measured optical aberrations of the eye when fitted with a particular test lens conforming to the FIG. 1 diagram.

FIG. 2 shows an additional step of the process which aims to refine the shape of the lens initially determined as explained above.

The lens L1 whose shape has been determined as previously described is used as a test lens. The lens L1 is therefore placed on the eye E to be corrected and the measurement unit 2 performs a new measurement of the optical aberrations of the optical system consisting of the eye E and the lens L1. The result of these optical aberration measurements is supplied by the measurement unit 2 in the form of a digital data file and is transmitted to the electronic calculator unit 3 as indicated by the arrow F2' in FIG. 2.

The electronic calculator unit 3 then recalculates the configuration of the front face of the lens from the data supplied to it by the unit 2 for measuring the optical aberrations and the data relating to the initially determined shape of the lens L1, which it holds in memory. The electronic calculator unit 3 then supplies a file of digital data representative of the corrected shape of the front face of the lens and the shape of the rear face of the lens, which has not changed. The file is transmitted to the fabrication unit 4, as symbolized by the arrow F3' in FIG. 2.

The fabrication unit 4 then fabricates a lens L2 whose front face is corrected relative to that of the test lens L1.

The lenses obtained preferably have ballast type stabilizing means, lower truncation, palpebral bosses of the type described in patent FR 2 760 853, top or bottom lightenings, or a combination of said means. The lenses obtained advantageously have markings outside the optical area. See, for example, patent FR 2 777 093.

The markings enable the clinician to verify correct positioning of the lens. They also indicate a reference mark for lens inspection instruments.

Figure 3:
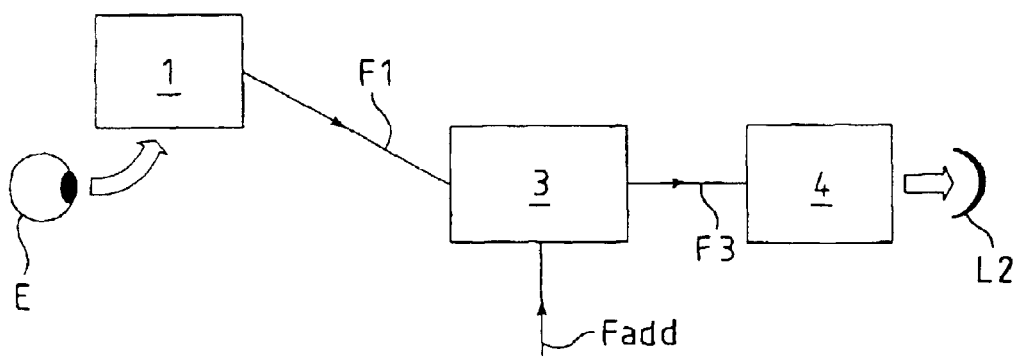
FIG. 3 is a diagram showing a system for fabricating a contact lens using a simplified second embodiment of the method and system according to the invention for determining the shape of a lens, in which the measurements of the topography of the cornea and the optical aberrations of the eye to be corrected are carried out in a single step and entirely by the unit for measuring the topography of the cornea.

FIG. 3 shows a simplified embodiment of a system for fabricating contact lenses using a system and a method in accordance with the invention to determine the shape of the lenses. This simplified embodiment is aimed at situations in which the ocular aberrations of the eye to be corrected stem essentially from defects in the shape of the cornea. In its essentials, the FIG. 3 system corresponds to the FIG. 1 system and the same parts are designated by the same reference numbers. In this embodiment, the optical aberrations of the eye E are no longer measured as such by the measurement unit (which is therefore omitted in this embodiment), but are simply deduced from the corneal topography measured by the measurement unit 1 by calculations effected by the software of the electronic calculator unit 3. The other parts of the system and steps of the process are identical to those previously described with reference to FIGS. 1 and 2.

There is claimed:

1. A method of determining the shape of an ophthalmic contact lens for correcting optical aberrations of an eye, which method includes the steps of:

measuring the optical aberrations of the eye to be corrected, and determining the shape of the front face of said lens from the measured optical aberrations of the eye to be corrected in order to correct said aberrations, measuring the topography of the cornea of the eye to be corrected, and determining the shape of the rear face of the lens from the measured topography of the cornea in order to limit the generation of unwanted aberrations when the lens is placed on the eye, and in which method, to determine the shape of the front face of the lens, data relating to the shape determined for the rear face of the lens is combined with the measured optical aberrations of the eye.

2. The method claimed in claim 1, wherein the topography of the cornea of the eye to be corrected and the aberrations of said eye to be corrected are measured in a common spatial frame of reference.

3. The method claimed in claim 2, wherein the common spatial frame of reference includes a first axis coincident with the main line of vision of the eye to be corrected.

4. The method claimed in claim 3, wherein the common spatial frame of reference includes a horizontal second axis orthogonal to the first axis and a third axis orthogonal to the first and second axes.

5. The method claimed in claim 1, which, to refine the initially determined shape of the lens, further includes the steps of:

fabricating a test lens having front and rear faces conforming to those determined by the aforementioned steps, measuring in vivo the optical aberrations of the optical system comprising the eye to be corrected fitted with the fabricated test lens, and correcting the shape of the front face of the lens on the basis of data relating to the initially determined shape of the test lens and the new measured optical aberrations of the eye fitted with the test lens.

6. The method claimed in claim 1, wherein the subjective refraction of the patient whose eye is to be corrected is taken into account in determining the shape of the front face of the lens.

7. The method claimed in claim 6, wherein the subjective refraction power is substituted by calculation for the objective refraction power contained in the data resulting from measuring the ocular aberrations of the eye.

8. The method claimed in claim 1, wherein the refractive index of the material of the lens is taken into account in determining the shape of the front face of the lens.

9. The method claimed in claim 1, wherein additional specific optical correction data that is combined with the measured optical aberrations is taken into account in determining the shape of the front face of the lens.

10. The method claimed in claim 9, wherein the additional data introduces a complex multifocal correction if the eye to be corrected suffers from presbyopia.

11. The method claimed in claim 1, wherein mechanical characteristics of the material of the lens are taken into account in determining the shape of the rear face of the lens.

12. The method claimed in claim 11, wherein the mechanical characteristics of the material of the lens taken into account are the constants of elasticity and viscosity of the material.

13. The method claimed in claim 1, wherein the means provided for fabricating the lens and the limitations imposed by said means on the possible shape of the front and rear faces of the lens are taken into account in determining the configurations of the front and rear faces of the lens.

14. The method claimed in claim 1, wherein the step of measuring the aberrations of the eye to be corrected coincides with the step of measuring the topography of the cornea of said eye to be corrected, which aberrations are deduced by calculation from the measured topography of said cornea.

15. A system for implementing the method claimed in claim 14, which system includes:

a measuring unit for measuring the topography of the cornea of the eye to be corrected and delivering digital data representative of that topography, and an electronic calculator unit adapted to estimate the aberrations produced by the cornea from the data supplied by the measurement unit for measuring the topography of the cornea and to determine the shapes of the front and rear faces of the lens from data supplied to it by the measurement unit for measuring the topography of the cornea and the estimated aberrations and to deliver digital data representative of those shapes.

16. A system for implementing the method according to the invention, which system includes:

a measuring unit for measuring the topography of the cornea of the eye to be corrected and delivering digital data representative of that topography, a measuring unit for measuring the aberrations of the eye to be corrected and delivering digital data representative of those aberrations, and an electronic calculator unit adapted to determine the shapes of the front and rear faces of the lens from data supplied to it by the measurement unit for measuring the topography of the cornea of the eye to be corrected and the measurement unit for measuring the aberrations of said eye to be corrected and to deliver digital data representative of those shapes.

17. The system claimed in claim 16, wherein the units for measuring the topography of the cornea and the aberrations use a common spatial frame of reference.

18. The system claimed in claim 17, wherein the common spatial frame of reference includes a first axis coincident with the main line of vision of the eye to be corrected.

19. The system claimed in claim 18, wherein the common spatial frame of reference includes a horizontal second axis orthogonal to the first axis and a third axis orthogonal to the first and second axes.

20. The system claimed in claim 16, which includes a fabrication unit for fabricating a lens from data supplied to it by the electronic calculator unit.

* * * * *